United States Patent [19]

Park et al.

[11] Patent Number: 4,640,941

[45] Date of Patent: Feb. 3, 1987

[54] HYDROGELS CONTAINING SILOXANE COMONOMERS

[75] Inventors: Joonsup Park; Joseph J. Falcetta, both of Arlington, Tex.

[73] Assignee: Alcon Laboratories, Fort Worth, Tex.

[21] Appl. No.: 816,766

[22] Filed: Jan. 7, 1986

Related U.S. Application Data

[63] Continuation-in-part of Ser. No. 801,259, Nov. 23, 1985.

[51] Int. Cl.$^4$ .................. A61K 6/10; C08L 43/00; C08L 43/04; C08F 230/08
[52] U.S. Cl. .................................. 523/107; 524/547; 524/806; 526/264; 526/279
[58] Field of Search ............... 523/107; 526/279, 264; 524/806

[56] References Cited

U.S. PATENT DOCUMENTS

| | | | |
|---|---|---|---|
| 3,220,960 | 11/1965 | Wichterle et al. | 260/2.5 |
| 4,095,877 | 6/1978 | Stoy et al. | 351/160 |
| 4,130,706 | 12/1978 | Plamback, Jr. | 526/245 |
| 4,139,513 | 2/1979 | Tanaka et al. | 260/29.6 TA |
| 4,182,822 | 1/1980 | Chang | 526/264 |
| 4,246,389 | 1/1981 | LeBoeuf | 526/279 |
| 4,343,927 | 8/1982 | Chang | 526/262 |
| 4,433,111 | 2/1984 | Tighe et al. | 525/326.1 |
| 4,436,887 | 3/1984 | Chromecek et al. | 526/263 |
| 4,440,919 | 4/1984 | Chromecek et al. | 526/263 |
| 4,451,630 | 5/1984 | Atkinson et al. | 526/261 |
| 4,492,776 | 1/1985 | Atkinson et al. | 526/261 |
| 4,528,325 | 7/1985 | Ofstead | 525/60 |
| 4,550,139 | 10/1985 | Arkles | 523/107 |

*Primary Examiner*—Herbert J. Lilling
*Attorney, Agent, or Firm*—James A. Arno; Gregg C. Brown

[57] ABSTRACT

Hydrogel polymeric material, suitable for preparing optical devices such as contact lenses. The material is of improved oxygen permeability and mechanical properties in comparison with conventional hydrogels. It comprises, in addition to the hydrogel material, from about 5% to about 60% by weight of a siloxane comonomer containing both an aromatic ring and vinyl functionality. Its cooperation and combination of performance characteristics with traditional hydrogel forming monomers provides a very useful polymeric material for making lenses of the soft hydrogel type.

21 Claims, No Drawings

HYDROGELS CONTAINING SILOXANE COMONOMERS

CROSS REFERENCE TO A RELATED APPLICATION

This application is a continuation-in-part of our earlier filed application by Park et al., entitled NEW SILOXANE MONOMERS FOR OPHTHALMIC APPLICATIONS, Ser. No. 801,259, filed Nov. 23, 1985.

BACKGROUND OF THE INVENTION

The present invention combines a class of novel siloxane monomers which contain an aromatic ring and vinyl functionality, as disclosed and claimed in our earlier application, with hydrogel forming monomers to form a polymeric hydrogel of improved oxygen permeability and mechanical properties.

It is important and essential that the cornea have access to atmospheric oxygen in order that an oxygen-carbon dioxide exchange can occur. Put another way, without constant eye exposure to the atmosphere, a state of oxygen edema can occur within the eye, which is potentially capable of causing damage. Thus, hard contact lenses, while having many practical advantages, generally are not altogether satisfactory because they most often have poor oxygen permeability.

Recently soft contact lenses, including the hydrogel type, have captured a significant market share. However, soft contact lenses are also not without disadvantages. Soft contact lenses generally have excellent eye comfort. However, soft lenses also readily attract and accumulate foreign debris, necessitating frequent cleaning. In addition, mechanical properties are often poorer with soft lenses.

Hydrogels are usually defined as natural or synthetic polymeric systems that contain approximately from about 10% to about 90% water in an equilibrium state. In general the physical properties of hydrogels are determined to a large extent by their water content. Due to their excellent biocompatability there has been extensive interest in hydrogels as biomedical devices. Thus there have been investigations on the use of hydrogels as contact lenses, intrastromal implants, intraocular lenses, coatings on numerous devices, membranes of several types, tissue replacement, ureter prosthesis, breast augmentation, etc. To date, the most commercial success has been found in the field of ophthalmology, and most particularly, soft contact lenses.

Hydrogel type contact lenses have been known, since at least as early as Wichterle et al, U.S. Pat. No. 3,220,960 which discloses a hydrogel which involves a hydrated polymer of an hydroxyalkyl acrylate or methacrylate cross-linked with a corresponding diester. Such gels may contain from about 10% to about 90% by weight water, preferably from about 30% to about 50% by weight water. Of the monomers used to prepare such hydrogels, 2-hydroxyethyl methacrylate is most commonly used. The equilibrium water content of lightly cross-linked poly (2-hydroxyethyl methacrylate) is about 40%. These hydrogels are often referred to as low water content hydrogels. Low water content hydrogels generally do not have as high an oxygen permeability as higher water content gels.

Another commonly used hydrogel system is based on copolymers of vinyl pyrrolidone and methyl methacrylate. The equilibrium water content of these hydrogels can vary widely as a function of the ratio of vinyl pyrolidone to methyl methacrylate. However, most hydrogels of commercial interest have a water content in the 70% to 80% by weight range. These hydrogels are often referred to as high water content hydrogels.

As a general rule the low water content hydrogels have acceptable mechanical properties for application as a soft contact lens. However, they do not have acceptable oxygen permeability (DK) to be used as an extended wear contact lens. Also, as a general rule the high water content hydrogels appear to have acceptable oxygen permeability for application as an extended wear contact lens but have poor mechanical properties, i.e., are not easily formed into stable lenses, are tearable, sometimes lack visual acuity, and are easily damaged.

For many other biomedical applications it is also apparent that the utility of hydrogels have been limited by a lack of suitable mechanical properties. Accordingly, there is a real and continuing need to develop hydrogels which have improved mechanical properties and maintain the other desirable features of hydrogels such as biocompatibility, softness, transparency, and permeability to oxygen and other metabolites. The primary object of this invention is to fill this need.

It is more specific objective of the present invention to prepare hydrogel type contact lenses of improved mechanical properties which have good optical properties and acceptable oxygen permeability.

It is another specific objective of this invention to develop a hydrogel, which even at the lower water content levels, i.e. 40% to 50%, has good oxygen permeability.

These more specific objectives are achieved by the copolymerization of a hydrogel forming monomer (or monomers) and a novel class of siloxane monomers characterized by containing both an aromatic ring functionality and vinyl functionality at certain stereo-directing positions, which can be employed as a monomer for preparing copolymers useful as materials to form making a wide variety of types of biomedical products including soft, hydrogel type lenses, and ocular implants.

The method and means of accomplishing each of the above objectives, as well as others, will become apparent from the detailed description of the invention which will follow hereinafter.

SUMMARY OF THE INVENTION

Certain siloxane monomers which contain both an aromatic ring and vinyl functionality are provided in combination with hydrogel forming monomers to form a hydrogel type polymeric material useful for making improved hydrogel type biomedical products. The siloxane monomer is used in an amount of from about 5% to about 60% by weight of the polymeric forming material and the hydrogel comonomer in about 40% to about 95% by weight of the polymeric material. The resulting polymers can be shaped into contact lenses of excellent oxygen permeability and improved machineability when compared with conventional hydrogel type lenses. The lenses are substantially inert to the eye, transparent, and provide good visual clarity and sharpness of image.

DETAILED DESCRIPTION OF THE INVENTION

Polymer hydrogels are widely used for biomedical application such as contact lenses and a large number of hydrogels of this type are based on the polymers described in U.S. Pat. No. 3,220,960 (Wichterle), whose disclosure as it relates to hydrogel monomers is incorporated herein by reference. Wichterle's polymers are hydroxy (lower alkyl $C_1$ to $C_8$) methacrylates or acrylates, cross-linked with a small percentage of the corresponding diester, e.g., ethylene glycol dimethacrylate (EGDMA). Polymers based upon hydroxyethyl methacrylate (HEMA) and cross-linked with EGDMA can be hydrated to form clear hydrogels having good mechanical properties.

As earlier mentioned, a degree of cross-linking in a copolymer is necessary to form a three dimensional polymer network structure. Typically one uses about 0.1% by weight of the composition to about 5% by weight of the composition of cross-linking comonomer. Various cross-linking comonomers may be employed such as glycol diacrylates, glycol dimethacrylates, like EGDMA including ethylene and propylene glycol diacrylates and dimethacrylates, polyethylene glycol diacrylates and dimethacrylates, allyl methacrylates, etc.

According to one aspect of the present invention there is provided a hydrogel which comprises a copolymer of hydroxy lower $C_1$ to $C_8$ alkyl methacrylate or acrylate with certain hereinafter described novel siloxane comonomers, with the amount of siloxane comonomer being from about 5% to about 60% by weight of the composition, and the amount of hydroxy lower alkyl methacrylate or acrylate being from about 40% to about 95%, preferably from about 70% to about 90% and correspondingly the amount of siloxane monomer from about 10% to about 30%. These percentages are on a total polymer weight basis and exclude added water.

The copolymerizable hydroxy lower alkyl $C_1$ to $C_8$ alkyl methacrylate or acrylate need not be described herein in detail, such hydrogel forming monomers being well-known and described previously in the earlier incorporated-by-reference Wichterle U.S. Pat. No. 3,220,960. As those skilled in the art know, the hydrogel monomer may also contain other comonomers such as vinyl pyrrolidone. The amount of the hydrogel monomer has previously been specified.

In addition to the siloxane comonomer, hereinafter described in detail, and the hydrogel, the polymeric formulations of this invention especially useful for forming hydrogel type soft contact lenses also typically will comprise from 0.1% to 5% cross-linker, and from 0% to about 40% of an added hydrophobic comonomer material.

The siloxane comonomer material, used in forming the polymers in conjunction with the hydrogel is a monomer containing both an aromatic ring and vinyl functionality having the following formula (I):

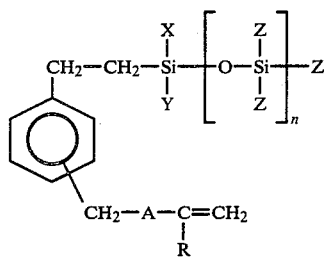

where
(1) "A" is selected from the group consisting of:

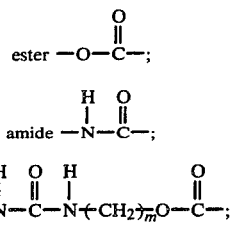

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

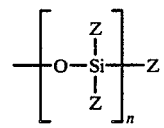

(5) Z is selected from the group consisting of $C_1$ to $C_5$ alkyl groups and phenyl groups; and
(6) n is an integer from zero to five.

It is not known precisely why the siloxane monomer of the present invention has a wide range of other monomer compatability, allowing it to be useful in making soft contact lenses, but it does. Without being bound to any theory, it is believed that perhaps its wide compatability is achieved because within the structure there is a synergistic relationship between the unique combination of functional groups and their spatial relationship to each other, giving the desirable properties. It is believed the presence of the aromatic ring contributes to a desirably higher index of refraction, on the order of 1.4515; the presence of the siloxane moiety provides for oxygen permeability; and, the presence of the vinyl functionality provides for good overall polymerization properties, without adversely impacting other desirable properties, especially oxygen permeability. In some instances where "A" in formula [I] is a urea derivative, the urea functionality provides for special desirability in preparing compatible hydrogel type lenses.

The increase in index of refraction of hydrogels prepared from these novel siloxane monomers is of significant importance in increasing the oxygen transported through a contact lens. For specified optical parameters a higher index of refraction will result in a contact lens of a reduced thickness. Therefore, since oxygen transport is inversely proportional to thickness, the oxygen transport is increased.

The precise manner of preparing the siloxane monomers of the present invention need not be described in detail herein, it having been described in our earlier cross-referenced parent application Ser. No. 801,259, filed Nov. 23, 1985.

Comonomers useful for making hydrogel type contact lenses include the hydroxy alkyl acrylates and methacrylates; hydroxyethyl methacrylate (HEMA), hydroxyethyl acrylate, hydroxy-polyethoxy ethyl methacrylate and the like. Examples of another class of suitable hydrophilic monomers are the N-vinyl heterocyclic monomers, suitable examples of such monomers being N-vinyl-2 pyrrolidone, N-vinyl pyridine and N- vinyl-ε-caprolactam. Also another class of hydrophilic monomers are the polymerizable olefinic acids and amides; suitable examples being acrylic acid, methacrylic acid, itaconic acid, fumaric acid, maleic acid, crotonic acid, acrylamide, methacrylamide and N-(1,1-dimethyl-3-oxobutyl acrylamide). Another suitable group of hydrophilic monomers are the lower alkyl vinyl ethers such as methyl and ethyl vinyl ether.

Other compatible mechanical property modifying monomers can be utilized to change the softening temperature and hardness and to improve machineability of the copolymer. Generally, these are somewhat hydrophobic monomers and preferred are the olefinically unsaturated polymerizable monomers with one polymerizable double bond per molecule. Suitable examples of such monomers are the linear or branched $C_1$ to $C_{10}$ alkyl esters of acrylic and methacrylic acid such as methyl acrylate, ethyl acrylate, butyl acrylate, 2-ethylhexyl acrylate, methyl methacrylate, ethyl methacrylate, butyl methacrylate, 2-ethylhexyl methacrylate, and the like monomers. Cycloalkyl acrylates and methacrylates may also be suitable as would such monomers as 2-ethoxyethyl methacrylate. Examples of other suitable hydrophobic monomers useful as compatible mechanical property modifiers are the vinyl ethers such as butyl vinyl ether and vinyl acetate, vinyl chloride, vinyl propionate, isoprene, vinyl carbazole, and styrene monomers other than those defined above for the main monomer which are styrenes, including alkoxy styrenes, e.g., methoxy and ethoxy sytrene, halogenated styrenes, hydroxyalkyl styrenes, alkoxy alkyl styrenes, and polyalkoxyether sytrenes.

The properties of hydrogels containing the siloxane comonomers are unique and unexpected. There have been many attempts in the prior art to improve the mechanical properties of hydrogels and still maintain acceptable oxygen permeability. However, these have been restricted to specific systems and are not based on the use of a comonomer that can improve the mechanical properties of hydrogels via incorporation by a copolymerization mechanism. Thus for example, Ofstead in U.S. Pat. No. 4,528,325 claims hydrogels of high strength based on the solvolysis of copolymers of vinyl trifluoroacetate (VTA) and up to 5% of certain comonomers such as vinyl esters or disubstituted ethylene monomers. These copolymers appear to have improved mechanical properties, however, unlike the HFIS copolymers they require the extra step of a reaction on a polymer and of course are very limited in compositions as they require the presence of at least 95% vinyl trifluoroacetate.

Another attempt at preparing high strength hydrogels is that of Stoy et al, is exemplified by U.S. Pat. No. 4,095,877. In this technique polymers or copolymers containing acrylonitrile are hydrolyzed to form high strength hydrogels. This technique also requires a reaction on a polymer and is far more limited in its scope than the present use of novel siloxanes to improve the strength and maintain acceptable oxygen permeability of hydrogels of varying compositions. Thus it can be seen that the copolymers of the present invention have distinct advantages. In short, while there are numerous reported attempts to improve mechanical properties and oxygen permeability that involve very specific hydrogel systems or a very narrow range of compositions, see e.g. U.S. Pat. Nos. 4,492,776, 4,451,630, 4,440,919, 4,436,887, and 4,433,111, none of these patents describe systems that have the wide applicability or range of mechanical properties and oxygen permeability values that are found with hydrogels based on copolymers incorporating the siloxane of our earlier cross-referenced parent application. It can thus be seen that the present hydrogels not only may improve mechanical properties and oxygen permeability but also are advantageous in the wide range of hydrogels that can be prepared.

The invention will be further described in connection with the following examples which are given for purposes of illustration and should not be construed as limiting on the invention. All parts and percents referred to herein are on a weight basis.

EXAMPLES OF PREPARING THE SILOXANE COMONOMER

Example 1

Synthesis of tris (trimethylsiloxy) silane-m,p-chloromethyl phenylethane

A catalyst solution is prepared by adding, with stirring, 23.8 g. of concentrated sulfuric acid to a solution of 11.6 g. of ethanol in 16.5 ml of distilled water.

To a 500 ml round bottom flask that is situated on an ice batch, a mixture of 43.6 g. (0.33 mole) of trimethylacetoxysilane and 27.4 g. (0.1 mole) of trimethoxysilane-m,p-chloromethyl) phenylethane is added. To this mixture 9.1 ml of the catalyst solution is added in a dropwise manner over a time period of 30 minutes.

The reaction mixture is vigorously stirred for three days at room temperature. After separation, the organic layer is neutralized with sodium bicarbonate, washed with water and dried over magnesium sulfate.

A yield of 31 g. (69.2%) of a slightly yellow liquid having an index of refraction of 1.4515 is obtained at 120°–135° C. (0.3–0.4 mm).

The identity of the compound was confirmed by the infrared spectrum and nmr spectrum [7.1 ppm (m,4H); 0.0 ppm (s,27H)].

Example 2

Synthesis of tris (trimethylsiloxy) silane(m,p-methacryloxymethyl)phenylethane

A mixture of 13.4 g. (3.0 mmole) and 3.6 g. (3.3 mmole) of sodium methacrylate in 150 ml of dimethylformamide was stirred at 125° C. for one hour. After cooling with an ice bath, 100 ml of distilled water was added. This reaction mixture was then extracted four times with 100 ml volumes of ethyl acetate. The combined organic layer is washed 3 times with 50 ml of a saturated sodium chloride solution and dried over anhydrous magnesium sulfate. After stripping off the low boiling components by vacuum distillation the final product was obtained at 120°–129° C. (0.1 mm) in a yield of 53.4%.

The identity of the compound was proven by the infrared spectrum and nmr spectrum [7.1 ppm (m,4H), 6.0 and 5.4 ppm (2 broad s,2H), 0.0 ppm (s,27H)].

Example 3 Synthesis of tris (pentamethyl disiloxy) silane(m,p-methacryloxymethyl)phenylethane Using a procedure similar to that given in Examples 1 and 2, trimethoxysilane(m,p-chloromethyl)phenylethane was reacted with pentamethylacetoxydisiloxane to form tris (pentamethyl disiloxy)-(m,p-chloromethyl) phenylethane in 44% yield. This compound was then reacted with sodium methacrylate in dimethylformamide solution to give a 83.9% yield of tris (pentamethyl disiloxy) silane-m,p-methacryloyloxymethyl phenylethane.

The identity of the compound was confirmed by the infrared spectrum; 1730 cm$^{-1}$ (C=O), 1640 cm$^{-1}$ (CH$_2$=), 1615 cm$^1$ (aromatic) and 1070 cm$^{-1}$ (Si—O—) and nmr spectrum; 7.1 ppm (m,4H); 5.9 and 5.3 ppm (2 broad s,2H); 1.8 ppm (s,3H); 0.0 ppm (broad s,45H).

Example 4

Synthesis of trimethylsiloxy-dimethylsilane-(m,p-methacryloxymethyl)phenylethane Trimethylsiloxyl-dimethylsilane(m,p-chloromethyl)-phenylethane was synthesized by the reaction of pentamethyldisiloxane and vinyl benzyl chloride in the presence of chloroplatinic acid. This compound was then reacted with sodium methacrylate in dimethylformamide using procedures similar to those given in Example 2 to form trimethylsiloxyl-dimethylsilane(m-p-methacryloxymethyl)phenylethane in a 50.7% yield. [B.P. 102° C. (0.1 mm)].

The identity of the compound was confirmed by the infrared spectrum; 1730 cm$^{-1}$ (C=O), 1640 cmhu −1 (CH$_2$=), 1615 cm$^1$ (aromatic) 1070 cm$^{-1}$ (Si—O—) and the nmr spectrum; 7.1 ppm (m,4H); 5.9 and 5.3 ppm (broad s,2H), 5,0 ppm (s,2H), 0 ppm (2s,15H).

Example 5

Synthesis of bis (trimethylsiloxy) methylsilane(m,p-methacryloxymethyl)phenylethane Using the procedure set forth in Example 4, bis (trimethylsiloxy) methyl(m,p-methacryloxymethyl)phenylethane was prepared in a yield of 54.7%. [B.P. 104°–124° C. (0.1–0.2 mm)].

The identity of the compound was confirmed by the infrared spectrum; 1730 cm$^{-1}$ (C=O), 1640 cm$^{-1}$ (CH$_2$=), 1070 cm$^{-1}$ (Si—O—) and the nmr spectrum; 7.1 ppm (m,4H); 5.9 and 5.4 ppm (2 broad S,5H), 5.0 ppm (s,2H), 1.8 ppm (s,3H), 0 ppm (2s,21H).

Example 6

Synthesis of Tris (trimethylsiloxy) silane(m,p-3-N-methacryloxymethylureido-1-N-methyl)phenylethane Tris (trimethylsiloxy) silane(m,p-azidomethyl)phenyl ethane was prepared by the reaction of 17.9 g. (40 mmole) with 2.80 g. (44 mmole) of sodium azide in 100 ml of methanol under reflux for four hours. After evaporation and washing with 100 ml of distilled water the residue was extracted three times with 100 ml of distilled water the residue was extracted three times with 100 ml portions of ethyl acetate. The combined extracts were washed twice with 50 ml distilled water each time, dried over anhydrous magnesium sulfate and evaporated in vacuo. The reaction product was obtained in 96.6% yield (17.2 g.), b.p. 120°–125° C. (0.4 mm).

Tris (trimethylsiloxy) silane(m,p-aminomethyl)phenylethane was prepared by the catalytic hydrogenation of tris (trimethylsiloxy) silane(m,p-azidomethyl)phenylethane.

To a Parr hydrogenation apparatus (500 ml capacity) were added, 16.3 g. (36 mmole) of tris (trimethylsiloxy) silane(m,p-azidomethyl)phenylethane, 2.6 g. acetic acid, 250 ml isopropanol and 0.87 g. of 5% palladium/charcoal. A cycle of hydrogenation at 5 psi for 15 min., evacuation and hydrogenation at 5 psi for 15 min. is repeated twice. The reaction mixture is filtered with the aid of Celite and the low boiling organics evaporated. The resulting liquid is treated with a 50:50 mixture of 5% aqueous sodium carbonate:ethyl acetate and the organic layer is then dried over anhydrous sodium sulfate. Vacuum distillation yields 10.8 g. (70.7% yield) of tris (trimethylsiloxy) silane(m,p-aminomethyl) phenylethane, b.p. 145°–155° C. (0.1 mm).

The identity of the compound was confirmed by the infrared spectrum; 3350 cm$^{-1}$ (NH$_2$), 1070 cm$^{-1}$ (Si—O) and nmr spectrum; 7.0 ppm (m,4H), 3.8 ppm (s,2H), 1.6 ppm (s,2H), 0 ppm (s,27H).

Compound tris (trimethylsiloxy) silane(m,p-aminomethyl) phenylethane was then prepared from the reaction of tris (trimethylsiloxy) silane(m,p-aminomethyl) phenylethane with isocyanoethyl methacrylate. Compound tris (trimethylsiloxy) silane(m,p-aminomethyl)phenylethane (22.0 g., 51 mmole) was reacted with 10.6 g. (68 mmole) of isocyanoethyl methacrylate in 110 ml methylene chloride in the presence of 2,5-diphenyl-p-benzoquinone as an inhibitor. The isocyanoethyl methacrylate is added dropwise over a period of 30 minutes with stirring while the reaction mixture is cooled by an ice bath. At the end of this time the ice bath was removed and the reaction proceeded at room temperature for an additional 5½ hours. Concentrated ammonium hydroxide (2 ml) is then added. The organic layer is then washed with 40 ml distilled water three times and dried over anhydrous magnesium sulfate. Silica gel column separation with ethyl acetate-hexane as the eluent yielded 19.4 g. (65.0%) of tris (trimethylsiloxy) silane(m,p-3-N-methacryloxymethylureido-1-N-methyl)phenylethane.

The identity of the compound was confirmed by the infrared spectrum; 3380 cm$^{-1}$ (NH), 1730 cm$^{-1}$ (C=O), 1580 cm$^{-1}$ (NHCO), 1070 cm$^{-1}$ (—Si—O) and the nmr spectrum; 7.0 ppm (m,4H), 5.8 and 5.3 ppm (2s,2H), 4.8 ppm (m,2H), 4.1 ppm (m,4H), 3.3 ppm (5,2H), 1.8 ppm (s,3H), 0 ppm (s,27H).

Example 7

Synthesis of tris (trimethylsiloxy) silane(m,p-N-methacrylaminomethyl)phenylethane Methacryloyl chloride (2.92 g., 28 mmole) is added dropwise over a period of thirty minutes to a solution of 10.0 g. (23 mmole) of compound tris (trimethylsiloxy) silane(m,p-aminomethyl)phenylethane and 2.83 g. (28 mmole) triethylamine in 100 ml of chloroform on an ice bath. A trace amount of 2,5-diphenyl-p-benzoquinone is added as an inhibitor. After the addition of methacryloyl chloride is complete, the ice bath is removed and the reaction continued for a total of six hours. Concentrated ammonium hydroxide (2 ml) is then added. The organic layer is then washed with 40 ml distilled water three times and dried over anhydrous magnesium sulfate. Vacuum distillation was then employed to obtain a 38% yield of tris (trimethylsiloxy) silane(m,p-N-methacrylaminomethyl)phenylethane [b.p. 170°–175° C. (.15 mm)].

The identity of the compound was confirmed by the infrared spectrum; 3350 cm$^{-1}$ (NH), 1670 and 1640 cm$^{-1}$ (NHCO), 1070 cm$^{-1}$ (SI—O—) and nmr spectrum; 7.0 ppm (m,4H), 6.0 ppm (broad, 1H), 5.5 and 5.2 ppm (2 broad s,2H), 4.3 ppm (2s,2H), 1.8 ppm (s,3H), 0 ppm (s,27H).

Examples 8 through 10

Showing Siloxane Monomer Properties

Using the reactions described in Examples 1 through 7, the monomers shown in Table I were prepared:

TABLE I

| Example # | Monomer | nmr data |
|---|---|---|
| 8 | bis (trimethylsiloxy)methylsilane-(m,p-N—methacryloylaminomethyl)-phenylethane | 7.1 ppm (m,4H)<br>5.6 & 5.3 ppm (2s,2H) |
| 9 | bis (trimethylsiloxy) methylsilane(m,p-3-N—methacryloxyethylureido-1-N—methyl)phenylethane | 7.0 ppm (m,4H)<br>6.0 & 5.5 ppm (2s,2H)<br>4.8 (Broad $D_2O$ exchangeable)<br>4.2 & 4.1 ppm (2t,4H)<br>3.3 ppm (t,2H)<br>0 ppm (2s,21H) |
| 10 | tris (pentamethyldisiloxy) silane(m,p-3-N—methacryloxyethylureido-1-N—methyl)phenylethane | 7.0 ppm (m,4H)<br>5.9 & 5.7 ppm (2 broad s,2H)<br>1.8 ppm (s,3H) |

Examples 11 through 14

Copolymer Films Films of the copolymers listed in Table II were prepared between (4×4 in.) glass plates.

The glass plates were pretreated with dimethyldichlorosilane and hydrolyzed to silanize the surface. Masking tape is placed around the edges of a glass plate to control the film thickness (target thickness was usually 0.1 mm). The monomer mix was placed on a glass plate, the two plates secured together by means of a metal clip and the assembly placed in an oven at 50° C. for one and one half hour. At the end of this time the glass plate assembly was heated to 90° C. for an additional 90 minutes. The think film was then removed from the glass plate assembly and stored in distilled water (phosphate buffer, pH 7.4). For all of the copolymers listed in Table II, 1.0 weight % of USP 245 (2,5-dimethyl-2,5-diperoxy-2'-ethylhexoate hexane) was added.

The composition of each copolymer in mole per cent is: siloxane monomer 16.2%, methyl methacrylate 76.9%, methacrylic acid 5.4% and ethylene glycol dimethacrylate 1.5%.

Oxygen permeability (DK) was measured in a water/water cell using an $O_2$ Permeometer ® Model 101T. The units of DK are $cm^2/sec$ ($mlO_2$/ml mmHg)$\times 10^{-11}$.

TABLE II

| Example # | Copolymer based on | DK |
|---|---|---|
| 11 | tris (pentamethyl disiloxy) silane-m,p-methacryloyloxymethyl phenylethane | 54 |
| 12 | tris (trimethylsiloxy) silane-m,p-methacryloxymethyl phenylethane | 18 |
| 13 | pentamethyldisiloxy-m,p-methacryloxymethyl phenylethane | 8 |
| 14 | bis (trimethylsiloxy) methyl-m,p-methacryloyloxymethyl phenylethane | 2.4 |

Example 15

Copolymerization of tris (trimethylsiloxy) silane(m,p-methacryloxymethyl)phenylethane with methyl methacrylate and methacrylic acid Tris (trimethylsiloxy) silane(m,p-methacryloxymethyl) phenylethane 3.84 g. was added to a clean, dry 20 ml glass, screw top test tube along with 3.62 g. methyl methacrylate, 0.39 g. methacrylic acid, 0.16 g. ethyleneglycol dimethacrylate and 0.09 g. USP 245. After degassing with Argon the tube was capped and placed in an oil bath at 50° C. for one hour and then at 70° C. for 72 hours. It was then carried through an annealing cycle at 120° C. A hard, transparent button was obtained that could be machined to a contact lens using standard lathing and polishing techniques. The contact lens thus obtained has a DK of 18.

The following table summarizes some of the monomers which have been or can be prepared in accordance with the invention.

TABLE III

| Compound Name | A | R | X | Y | Z | n |
|---|---|---|---|---|---|---|
| tris(trimethylsiloxy)-silane-(m,p-methacryloxymethyl)-phenylethane | Ester | Methyl | $-OSi(CH_3)_3$ | * | $-CH_3$ | 1 |
| tris(pentamethyl disiloxyl silane-(m,p-methacryloxymethyl)phenylethane | Ester | Methyl | $-OSi(CH_3)_2$ | $OSi(CH_3)_3$* | $-OSi(CH_3)_3$ | 1 |
| tris(trimethylsiloxy)-silane-(m,p-N—methacrylaminomethyl)phenylethane | Amide | Methyl | $-OSi(CH_3)_3$ | * | $-CH_3$ | 1 |
| bis(trimethylsiloxy)methyl-silane-(m,p-N—methacrylaminomethyl)phenylethane | Amide | Methyl | $-CH_3$ | $OSi(CH_3)_3$ | $-CH_3$ | 1 |
| bis(trimethylsiloxy)methyl-silane-(m,p-methacryloxymethyl)phenylethane | Ester | Methyl | $-CH_3$ | $OSi(CH_3)_3$ | $-CH_3$ | 1 |
| trimethylsiloxy-dimethsilane-(m,p-methacryloxymethyl)phenylethane | Ester | Methyl | $-CH_3$ | * | $-CH_3$ | 1 |
| tris(pentamethyl disiloxyl silane-(m,p-3-N—methacryloxymethylureido-1-N—methyl)-phenylethane | Urea, m = 2 | Methyl | $-OSi(CH_3)_2$ | $OSi(CH_3)_3$* | $-OSi(CH_3)_3$ | 1 |
| tris(trimethylsiloxy)-silane-(m,p-3-N—methacryloxymethylureido-1-N—methyl)-phenylethane | Urea, m = 2 | Methyl | $-OSi(CH_3)_3$ | * | $-CH_3$ | 1 |

TABLE III-continued

| Compound Name | A | R | X | Y | Z | n |
|---|---|---|---|---|---|---|
| bis(trimethylsiloxy)methyl-silane-(m,p-3-N—methacryl-oxymethylureido-1-N—methyl)-phenylethane | Urea, m = 2 | Methyl | —CH₃ | OSi(CH₃)₃ | —CH₃ | 1 |

*Y and X are the same.

Those monomers prepared in Examples 2, 3 and 6, which are also shown in Table III, are preferred.

Example 16

The objective of Example 16 is to determine the effect of one of the preferred siloxane comonomers (tris urea) having the formula tris(trimethylsiloxy)-silane(m,p-3-N-methacryloxymethyl-ureido-1-N-methyl)phenylethane (Example 6) on the properties of HEMA hydrogels. Films were prepared as in Examples 11–14. The hydrogels were made, their DK measured, their water content measured, and their index of refraction measured. Table IV illustrates compositions A, B and C, respectively.

Oxygen permeability was measured as in Examples 11–14. Mechanical properties were measured using an Instron ® universal testing instrument, Model 1122. Tests were carried out with the test specimen in a water bath. The units of tensile strength and modulus are Kg/cm².

It can be seen that the oxygen permeability was similar to HEMA alone, even though the water content had been decreased from 35% to 20%. The mechanical properties in addition were noted to be improved. This composition is suitable and satisfactory for making a soft hydrogel type contact lens.

TABLE IV

|  | A | B | C |
|---|---|---|---|
| HEMA | 100 | 90 | 80 |
| Tris Urea | — | 10 | 20 |
| H₂O Content | 35% | 28% | 20% |
| DK | 9.8 | 7.6 | 10.0 |
| Tensile Strength (Kg/cm²) | 9.0 | 18 | 70 |
| % Elongation | 140 | 275 | 275 |
| Modulus (Kg/cm²) | 11 | 17 | 73 |

Example 17

In accordance with this example, HEMA, methacrylic acid (MA) copolymers were used as a model system to evaluate the impact of tris urea on oxygen permeability and mechanical properties of films. A stock solution of HEMA/MA in a 100/4 ratio was prepared. Tris urea was added in the proportions of 0%, 10%, 20% and 30%. The films were prepared as in Examples 11–14. Table V shows the results.

TABLE V

|  | Tris Urea Added | | | | HEMA |
|---|---|---|---|---|---|
|  | 0 | 10 | 20 | 30 | Example 4A |
| H₂O Content (%) | 68 | 58 | 52 | 41 | 35 |
| DK | 17 | 18 | 19 | 19 | 9.8 |
| Tensile Strength | 5.0 | 8.6 | 10.7 | 12.3 | 9.0 |
| Elongation (%) | 96 | 120 | 111 | 129 | 140 |
| Modulus | 6.3 | 11.6 | 17.4 | 22.3 | 11 |

It can be seen that the tris urea significantly increased the oxygen permeability of the HEMA based hydrogels, and at the same time the mechanical properties were improved.

Other suitable results can be obtained when the tris urea is replaced with other of the siloxane monomers shown in the earlier examples 1–15, in that hydrogel type lens materials of improved oxygen permeability and mechanical properties are obtained.

Example 18

This example demonstrates the preparation of a hydrogel type polymeric material suitable for making contact lenses, differing from those in Examples 16 and 17 in that the HEMA is removed and replaced with vinyl pyrrolidone type hydrogels to form compositions with a total water content of above 40%. A stock solution of methyl methacrylate/vinyl pyrrolidone in a 30/70 ratio was prepared. To this was added 0%, 15% and 25% tris urea. Rods were prepared following the procedure given in Example 15. The properties were obtained from discs. Table VI below shows the results.

TABLE VI

|  | 70 VP/30 MMA TRIS UREA ADDED | | |
|---|---|---|---|
|  | 0 | 15 | 25 |
| H₂O Content | 67% | 58% | 52% |
| DK | 28 | 28 | 28 |
| Index of Refraction | 1.3910 | 1.4090 | 1.4165 |
| Machineability | Similar to Standard Hydrogels | | |

It can be seen that incorporation of tris urea into a vinyl pyrrolidone copolymer significantly raises oxygen permeability. The following Table VII shows a comparison of oxygen permeability for hydrogels after the lens is hydrated with water. The first two presented in the Table represent siloxane HEMA copolymer, and secondly siloxane vinyl pyrrolidone copolymer. The next four compositions represent commercial hydrogel type lenses, and are designated as lenses 1–4.

TABLE VII

|  | Water Content | DK |
|---|---|---|
| Siloxane/HEMA Copolymer | 41% | 19 |
| Siloxane/VP Copolymer | 52% | 28 |
| Commercial Lens #1 | 39 | 8 |
| Commercial Lens #2 | 43 | 11 |
| Commercial Lens #3 | 55 | 14 |
| Commercial Lens #4 | 70 | 31 |

Again, it can be seen that a significant improvement in DK, that is oxygen permeability, is obtained by the hydrogel compositions of the present invention, in comparison with other now readily available commercial hydrogel type lenses.

It therefore can be seen that the invention accomplishes all of its stated objectives.

What is claimed is:

1. A hydrogel polymeric material comprising from about 40% to about 95% of hydrogel forming comonomer material, and from about 5% to about 60% by weight of a siloxane monomer having the formula:

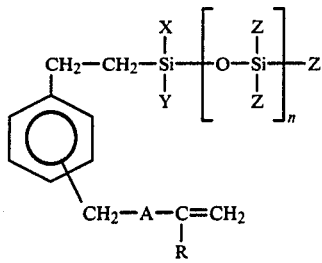

where
(1) "A" is selected from the group consisting of:

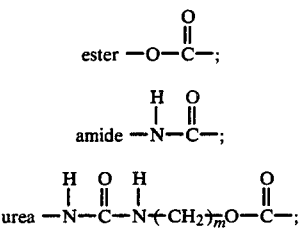

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

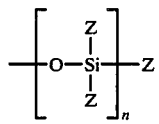

(5) Z is selected from the group consisting of $C_1$ to $C_5$ alkyl groups and phenyl groups; and
(6) n is an integer from zero to five.

2. The polymeric material of claim 1 wherein A is an ester group.

3. The polymeric material of claim 1 wherein A is an amide group.

4. The polymeric material of claim 1 wherein A is a ureido group.

5. The polymeric material of claim 1 wherein X and Y are methyl.

6. The polymeric material of claim 1 wherein W is trimethylsiloxyl.

7. The polymeric material of claim 1 wherein W is pentamethylsiloxyl.

8. The polymeric material of claim 1 wherein A is an ester group, R is methyl, X and Y are $OSi(CH_3)_3$, Z is methyl, and N is 1.

9. The polymeric material of claim 1 wherein the hydrogel forming monomer is a hydroxyalkyl acrylate or methacrylate of a lower $C_1$ to $C_8$ alkyl.

10. The polymeric material of claim 9 wherein the hydroxy alkyl monomer is hydroxy ethyl methacrylate.

11. The polymeric material of claim 9 wherein the hydroxy alkyl acrylate or methacrylate is from about 75% to about 90% by weight of the hydrogel forming comonomer material.

12. The polymeric material of claim 1 wherein the hydrogel forming monomer is N-vinyl pyrrolidone.

13. The polymeric material of claim 1 which includes from about 0.1% by weight to about 5% by weight cross-linking agent.

14. The polymeric material of claim 1 which includes from about 0% by weight to about 40% by weight of a property modifying organic hydrophobic monomer selected from the group consisting of $C_1$ to $C_8$ alkyl methacrylates and alkylates, cycloalkyl methacrylates and alkylates, styrene, t-butyl sytrene and other ring substituted styrenes.

15. The polymeric material of claim 14 wherein the hydrophobic monomer is methyl methacrylate.

16. The polymeric material of claim 15 wherein the methyl methacrylate is present in an amount of from 15% by weight to 30% by weight of said composition.

17. A contact lens of the hydrogel type having improved oxygen permeability and mechanical properties, comprising from 5% to 50% by weight of a siloxane monomer having the formula:

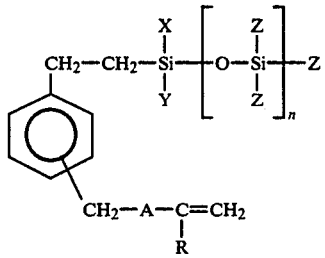

where
(1) "A" is selected from the group consisting of:

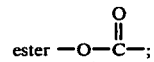
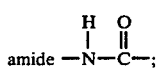
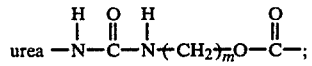

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

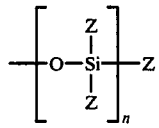

(5) Z is selected from the group consisting of $C_1$ to $C_5$ alkyl groups and phenyl groups; and
(6) n is an integer from zero to five; and
(7) from about 5% to about 50% by weight of a hydrogel forming comonomer.

18. The lens of claim 17 wherein the siloxane comonomer is tris (trimethylsiloxy) silane (m,p-3-N-methacryloxymethylureido-1-N-methyl) phenylethane.

19. The lens of claim 18 wherein the hydrogel forming comonomer is a hydroxyalkyl acryate or methacrylate of a lower $C_1$ to $C_8$ alkyl.

20. The lens of claim 19 which includes from 0.1% to 5% cross-linking agent and from 0% to 40% of a hydrophobic monomer.

21. An intraocular lens comprising the hydrogel polymeric material of claim 1.

* * * * *